United States Patent [19]

Joyce

[11] Patent Number: 4,597,562

[45] Date of Patent: Jul. 1, 1986

[54] APPARATUS FOR LOWERING AND RAISING AN ARTICLE

[75] Inventor: Edward D. Joyce, Ringwood, N.J.

[73] Assignee: F. W. Saybolt & Co. Inc., Kenilworth, N.J.

[21] Appl. No.: 550,266

[22] Filed: Nov. 9, 1983

[51] Int. Cl.⁴ .............................................. B66D 1/36
[52] U.S. Cl. ................................ 254/334; 73/864.31; 254/375; 254/413
[58] Field of Search ....................... 254/329, 334, 413; 73/864.31; 242/106; 403/DIG. 9; 269/95, 901; 248/231.5, 231.2, 225.31; 24/485, 457; 4/560-566

[56] References Cited

U.S. PATENT DOCUMENTS

| | | | |
|---|---|---|---|
| 711,068 | 10/1902 | McMahon | 269/95 X |
| 1,894,817 | 1/1933 | Ford | 73/864.31 X |
| 1,915,900 | 6/1933 | Moody | 254/334 |
| 2,580,130 | 12/1951 | Rowdon | 242/106 |
| 4,187,702 | 2/1980 | Benton | 248/231.5 X |
| 4,358,089 | 11/1982 | Metcalf | 254/413 X |
| 4,468,004 | 8/1984 | Shaver et al. | 254/325 |

FOREIGN PATENT DOCUMENTS 1932865  1/1971  Fed. Rep. of Germany ...... 254/334

Primary Examiner—Stuart S. Levy
Assistant Examiner—Katherine Matecki
Attorney, Agent, or Firm—Jordan and Hamburg

[57] ABSTRACT

An apparatus for lowering and raising a suspended article comprises a base, at least one holding means connected to the base adapted to locate and hold the base onto a desired structure, a suspension rod rotatably connected to the base, and winding means connected to the base or the suspension rod. The suspension rod extends upwardly from the base and includes a hanging device at an upper end thereof. The winding means windingly receives a cord extending downwardly through the hanging device of the suspension rod for lowering and raising the article attached to an end of the cord.

6 Claims, 7 Drawing Figures

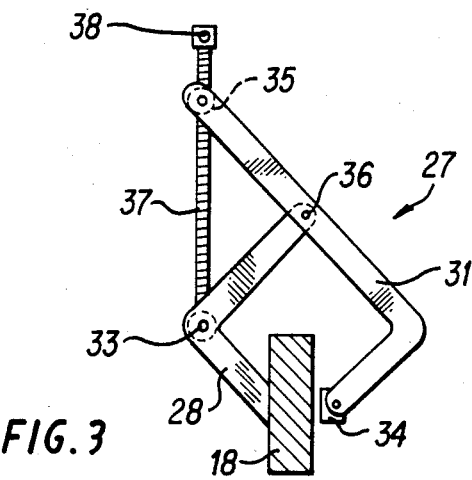
FIG. 3
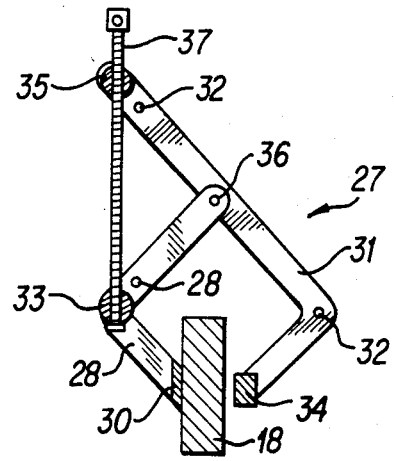
FIG. 4
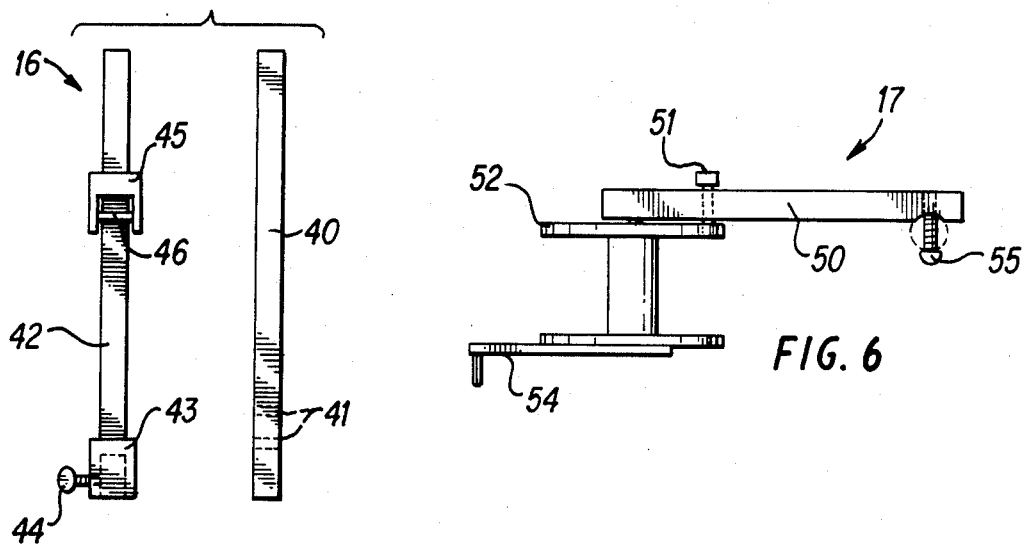
FIG. 5
FIG. 6
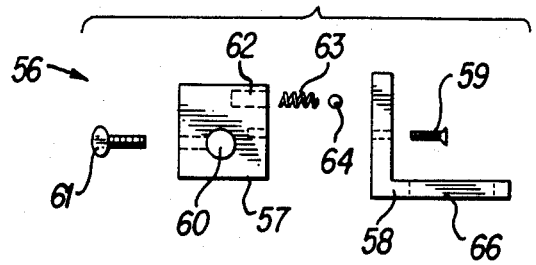
FIG. 7

4,597,562

APPARATUS FOR LOWERING AND RAISING AN ARTICLE

BACKGROUND OF THE INVENTION AND INFORMATION DISCLOSURE STATEMENT

The present invention relates to an apparatus for lowering and raising an article suspended by a cord. The term "cord" as employed herein is intended to encompass any pliable line, including, but not limited to, cords, ropes, strings, chains, cables and the like. In particular, the invention is directed to an apparatus for lowering and raising a container in the course of sampling a liquid in a tank. However, the invention is not limited to this purpose and may be used wherever it is desired to lower and raise an object.

A liquid material, such as a fuel oil or other petroleum distillate, is stored or held in a tank and is sampled, for example, prior to transfer of ownership, for inspection of quality or content thereof. For proper sampling, the liquid in a tank is to be collected from the bottom part and the upper part of the tank and levels therebetween in view of possible stratification of the liquid. In sampling the liquid, a special container which is known already in the art is attached to a cord and is inserted or led into the tank, for example, in the case of a tanker ship, through an ullage hatch situated on top of the tank. The cord is manipulated by hand to lower and raise the container.

In sampling, when the container is submerged into the liquid in a tank, the liquid in the tank adheres to the cord, so that when the container is raised after sampling the liquid, the hands and garment of a user get wet and dirty from the liquid. Further, when the liquid at the bottle of a large tank is sampled, it requires a great deal of labor for lowering and raising the container.

Therefore, an object of the invention is to provide an apparatus for lowering and raising a container suspended on a cord without directly manipulating the cord.

Another object of the invention is to provide an apparatus as stated above, which is portable and can be detachably connected to any size of an opening of a tank.

A further object of the invention is to provide an apparatus as stated above, which can be easily operated without a great deal of labor.

A still further object of the invention is to provide an apparatus as stated above, by which a user can be prevented from getting wet or dirty due to the liquid of the tank.

Further objects and advantages of the invention will be apparent from the following description of the invention.

SUMMARY OF THE INVENTION

In accordance with the present invention, there is provided an apparatus for lowering and raising an article suspended by a cord. The apparatus comprises a base, at least one holding means connected to the base adapted to locate and hold the base onto a desired structure a suspension rod rotatably connected to the base, and winding means connected to either the base or the suspension rod. The suspension rod extends upwardly from the base and includes a hanging device at an upper end thereof. The winding means windingly receives a cord extending downwardly through the handing device of the suspesnion rod for lowering and raising the article attached to an end of the cord.

The base comprises first and second base plates hingedly connected with each other, and positioning means connected to the first and second base plates to adjustably fix relative position therebetween. The positioning means comprises a fastening screw located in the first base plate, and a positioning plate having at least one elongated slot at one end. The positioning plate is rotationally connected to the second base plate at the opposite end of the slot and is fastened to the first base plate by the screw passing through the elongated slot. Consequently, when the screw is tightened, the relative position between the first and second base plates is determined.

Preferably, two holding means are provided respectively at the first and second base plates to firmly attach the base onto a desired structure. The holding means comprises a fixed member having a lower end connected to the base plate and an upper end extending upwardly from the lower end, a movable member rotationally connected at a middle portion thereof to the upper end of the fixed member and having an upper end and a lower end located near the base at the opposite side of the fixed member, and a tightening rod threadably engaging the upper end of the movable member and rotatably connected to the fixed member. Consequently, when the tightening rod is rotated, the lower end of the movable member moves close to and away from the base to thereby firmly grasp the structure therebetween.

The winding means comprises an arm connected to the suspension rod, a reel rotationally connected to the arm and having a grip for rotating the reel to wind the cord attached thereto, and locking means to prevent rotation of the reel.

The apparatus further includes a flash light holder so that sampling of the liquid can be done at night. The holder comprises a holding plate detachably connected to the suspension rod, and a supporting plate rotationally connected to the holding plate and having means to receive a flash light therein. Consequently, the flash light, when attached, can be oriented in any direction.

BRIEF DESCRIPTION OF THE DRAWINGS

FIG. 3 is a section view taken along line 3—3 in FIG. 2;

FIG. 4 is a section view taken along line 4—4 in FIG. 2;

FIG. 5 is a disassembled side view of the suspension section of the apparatus of FIG. 1;

FIG. 6 is a plan view of the winding section of the apparatus of FIG. 1; and

FIG. 7 is an exploded plan view of the flash light holder of the apparatus of FIG. 1.

DETAILED DESCRIPTION OF A PREFERRED EMBODIMENT

Figure 1:
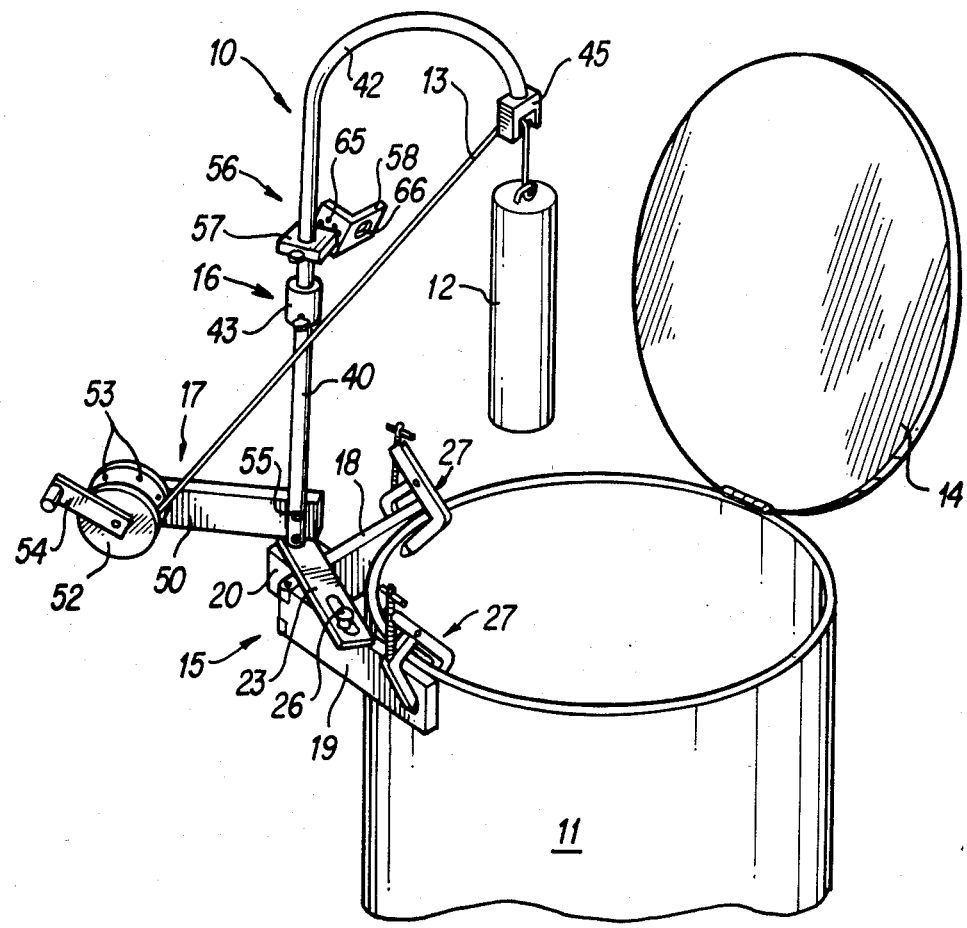
FIG. 1 is a perspective view of an apparatus in accordance with the present invention for showing the apparatus in use.

Referring to FIGS. 1-7, an apparatus 10 in accordance with the present invention is shown. In this particular embodiment, the apparatus 10 is designed to be attached to a ullage hatch 11 of the tank of an oil tanker for lowering and raising a receptacle 12, such as a liquid sampling device disclosed in U.S. Pat. No. 4,078,433, suspended by a cord 13 so that the oil in the oil tank is sampled. The ullage hatch 11 to which the apparatus 10 is detachably connected is located on top of the tank and is generally closed by a cover. When the oil sampling is required, the cover 14 is opened and the apparatus 10 is attached to the hatch 11. Then, the sampling is performed.

Basically, the apparatus 10 comprises a base section 15 to be attached to the hatch 11, a suspension section 16 connected to the base section 15, and a winding section 17 connected to the suspension section 16. The cord 13 is connected to the winding section 17 and extends through an end of the suspension section 16. When the winding section 17 is operated, the cord 13 extends from and retracts thereto.

Figure 2:
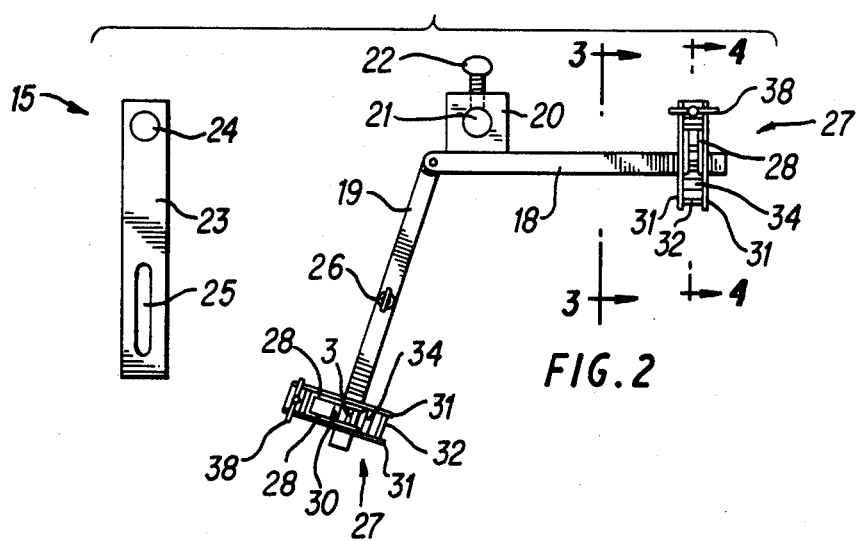
FIG. 2 is a disassembled plan view of the base section of the apparatus of FIG. 1.

The base section 15, as shown in FIGS. 1 and 2, comprises two base plates 18,19 hinged to be moved relative to each other, a supporter 20 connected to the plate 18. The supporter 20 includes a hole 21 to receive therein an end of a suspension section 16, and a screw 22 for securing the end of the suspension section 16 to the supporter 20 as explained further hereinafter.

The base section 15 further includes a positioning plate 23 having therein a hole 24 at one end and an elongated hole 25 at the other end thereof. The suspension section 16, when attached to the supporter 20, passes through the hole 24 of the positioning plate 23 so that the plate 23 can be rotatably connected to the plate 18 by means of the suspension section 16. The plate 19 is provided with a screw 26, and the screw 26, when attached to the plate 19, passes through the hole 25. Therefore, when the screw 26 is not tightened, the plates 18,19 can be rotated, but when the screw 26 is tightened, the relative position between the plates 18 and 19 is set and determined.

The base section 15 is further provided with two holding 1 means 27 connected to the plates 18,19, respectively, for attaching the apparatus 10 to the hatch 11. As clearly shown in FIGS. 3 and 4, the holding means 27 comprises fixed plates 28 connected parallel to each other by a pin 29 and an attachment 30, and movable plates 31 connected parallel to each other by two pins 32. The fixed plates 28 are firmly connected to the plate 18 or 19 at the attachment 30 and includes a rotatable member 33 rotatably situated therebetween. The movable plates 31 include therebetween a rotatable attachment 34 at a lower end and a rotatable threaded member 35 at an upper end thereof, and are rotatably connected to the fixed plates 28 by means of a pin 36. A tightening rod 37 with threads on an outer surface thereof engages the threaded member 35 and extends downwardly therefrom. The tightening rod 37 is provided with a tightening bar 38 at an upper end and is rotationally connected to the rotational member 33 at a lower end thereof. Therefore, when the tightening rod 37 is rotated, the attachment 34 of the movable plates 31 moves close to and away from the plate 18 or 19. Consequently, the base plates 18,19 can be firmly attached to the hatch 11 by tightening the holding means 27.

The suspension section 16 comprises, as shown in FIG. 5, a lower rod 40 having two holes 41 at a lower end and an upper rod 42 having a connecter 43 with a screw 44 at a lower end. The upper portion of the upper rod 42 is curved and includes at the upper end thereof a hanging device 45 connected thereto. The hanging device 45 includes a horizontal bar 46 to allow the cord 13 to pass above the bar 46.

When assembled, the lower end of the rod 40 passes through the hole 24 of the positioning plate 23 and is inserted into the hole 21 of the supporter 20. The rod 40 is secured to the supporter 20 by the screw 22. The connecter 43 of the rod 42 is disposed on the upper end of the rod 40, and the screw 44 is fastened to connect the rods 40, 42 together. The cord 13 wound at the winding section 17 passes above the bar 46 of the hanging device 45 and is oriented downwardly therefrom.

As shown in FIG. 6, the winding section 17 comprises an arm 50 with a stop pin 51 therein, and a reel 52 rotationally connected to the arm 50. The reel 52 includes a plurality of small openings 53 (FIG. 1) at a side wall adjacent to the arm to engage the stop pin 51, and a grip 54 for rotation of the reel 52. The arm 50 is connected to the rod 40 by means of screws 55 passing through the holes 41 of the rod 40, so that the base section 15, the suspension section 16 and the winding section 17 are integrally connected together.

As stated before, the cord 13 is wound on the real 52 and extends through the hanging deviee 45. The stop pin 51 is engaged with one of the openings 53 of the reel 52 to prevent rotation of the reel 52 when required, such as when the receptacle 12 is attached to or detached from the cord 13.

FIG. 7 shows a flash light holder 56 to be attached to the rod 42. The holder 56 may be connected to the rod 40 as well. When the oil sampling is performed at night, a flash light (not shown) may be supported by the holder 56.

The holder 56 comprises a holding plate 57 attached to the rod 42, and a supporting plate 58 rotationally connected to the holding plate 57 by a screw 59. The holding plate 57 includes a hole 60 and a screw 61 so that the rod 42 is disposed within the hole 60 and the plate 57 is fastened to the rod 42 by tightening the screw 61. The holding plate 57 further includes a blind hole 62 into which a spring 63 and a ball 64 are disposed. As shown in FIG. 1, the supporting plate 58 is provided with a plurality of small indentations 65 arranged in circular formation. When the supporting plate 58 is rotationally attached by the screw 59 to the holding plate 57, the ball 64 is urged by the spring 63 toward the supporting plate 58 and is engaged by one of the indentations 65. Therefore, the supporting plate 58 is rotationally held against the holding plate 57 to orient the flash light in the desired direction. The flash light is held in an opening 66 in the supporting plate 58.

When the apparatus 10 of the invention is used, the base section 15, the suspension section 16 and the winding section 17 are preassembled together, and the cord 13 is fully wound on the reel 52. The receptacle 12 may be attached to the end of the cord 13. In that case, the stop pin 51 should be engaged with the opening 53 to prevent rotation of the reel 52. Then, it is required to bring the apparatus 10 to the top of the tank.

After opening the cover 14, the screw 26 is loosened to adjust the angle between the plates 18 and 19 so that the tightening means 27 are surely located adjacent to the ullage hatch 11. Then, the tightening means 27 and the screw 26 are tightened to attach the apparatus 10 to the hatch 11. If the hanging device 45 is not properly located above the hatch 11, the rod 42 is turned relative to the rod 40 to adjust the location thereof.

Then the receptacle 12 is lowered down by rotation of the reel 52, and after sampling, the reel 52 is wound up to raise the receptacle 12. When the sampling is finished, the apparatus is detached from the hatch.

While the invention has been described with reference to a specific embodiment thereof, it is to be noted that the description is illustrative and the invention is limited only by the appended claims.

What is claimed is:

1. An apparatus for lowering and raising an article suspended by a cord, comprising
   a base including first and second base plates hingedly connected to each other, and positioning means connected to said first and second base plates to adjustably fix the relative position therebetween,
   two holding means connected to said first and second base plates respectively and adapted to locate and fix the first and second base plates onto a desired structure, each holding means including a fixed member having a lower end connected to the base plate and an upper end extending upwardly from the lower end, a movable member rotationally connected at the middle portion thereof to the upper end of the fixed member and having upper and lower ends, said lower end being located near the base plate at a side opposite the fixed member relative to the base plate, and a tightening rod threadably engaging the upper end of the movable member and rotatably connected to the fixed member so that when the tightening rod is rotated in the tightening direction, the upper end of the movable member is moved upwardly to cause the lower end of the movable member to move toward the base plate to thereby firmly grasp the structure between the movable member and the base plate,
   a suspension rod rotatably connected to one of the first and second base plates, said suspension rod extending upwardly from the base and having a hanging device at an upper end thereof, and
   winding means connected to said suspension rod, said cord being operably connected to the winding means at one end and extending downwardly through the hanging device of the suspension rod so that the winding means, when actuated, lowers and raises the articles suspended by the cord.

2. An apparatus according to claim 1, in which said suspension rod comprises a straight rod rotatably connected to one of the first and second base plate, and a curved rod rotatably connected to the straight rod, said hanging device being attached to said curved rod so that the hanging device can be located above the structure.

3. An apparatus according to claim 1, in which said winding means comprises an arm connected to said suspension rod, a reel rotatably connected to said arm and having a grip for rotating the reel to wind the cord attached thereto, and locking means to prevent rotation of the reel.

4. An apparatus according to claim 3, in which said locking means comprises a locking pin attached to said arm, said reel including at least one small hole adjacent to the arm, said locking pin, when required, being engaged with said small hole to prevent rotation of said reel.

5. An apparatus according to claim 1, further comprising a flash light holder including a holding plate detachably connected to said suspension rod, and a supporting plate rotationally connected to said holding plate and having means to receive a flash light therein, whereby the flash light can be oriented in any direction.

6. An apparatus according to claim 1, in which said positioning means comprises a fastening screw located in the first base plate, and a positioning plate having at least one elongated slot at one end, said positioning plate being rotationally connected to said second base plate at the opposite end of said slot and connected to said first base plate by said screw passing through the elongated slot, whereby when the screw is tightened the relative position between the first and second base plate is determined.

* * * * *